United States Patent [19]
McLeod et al.

[11] Patent Number: 6,093,205
[45] Date of Patent: Jul. 25, 2000

[54] SURGICAL IMPLANT

[75] Inventors: Alan Rory Mor McLeod, Somerset; Andre Jackowski, Birmingham, both of United Kingdom

[73] Assignee: Bridport-Gundry PLC c/o Pearsalls Implants, Taunton, United Kingdom

[21] Appl. No.: 09/104,422

[22] Filed: Jun. 25, 1998

[30] Foreign Application Priority Data

Jun. 25, 1997 [GB] United Kingdom .................. 9713330

[51] Int. Cl.$^7$ .................................................. A61F 2/44
[52] U.S. Cl. .............................................. 623/17; 606/61
[58] Field of Search ................................ 623/17; 606/61

[56] References Cited

U.S. PATENT DOCUMENTS

| | | |
|---|---|---|
| 3,867,728 | 2/1975 | Stubstad et al. . |
| 3,875,595 | 4/1975 | Froning . |
| 4,280,954 | 7/1981 | Yannas et al. . |
| 4,309,777 | 1/1982 | Patil . |
| 4,349,921 | 9/1982 | Kuntz . |
| 4,458,678 | 7/1984 | Yannas et al. . |
| 4,512,038 | 4/1985 | Alexander et al. . |
| 4,714,469 | 12/1987 | Kenna . |
| 4,759,766 | 7/1988 | Beuttner-Janz et al. . |
| 4,759,769 | 7/1988 | Hedman et al. . |
| 4,772,287 | 9/1988 | Ray et al. . |
| 4,863,476 | 9/1989 | Sheppard . |
| 4,863,477 | 9/1989 | Monson . |
| 4,880,429 | 11/1989 | Stone . |
| 4,904,260 | 2/1990 | Ray et al. . |
| 4,911,718 | 3/1990 | Lee et al. . |
| 4,932,969 | 6/1990 | Frey et al. . |
| 4,932,975 | 6/1990 | Main et al. . |
| 4,946,378 | 8/1990 | Hirayama et al. . |
| 4,955,908 | 9/1990 | Frey et al. . |
| 5,002,576 | 3/1991 | Fuhrmann et al. . |
| 5,007,934 | 4/1991 | Stone . |
| 5,047,055 | 9/1991 | Bao et al. . |
| 5,108,438 | 4/1992 | Stone . |
| 5,123,926 | 6/1992 | Pisharodi . |

(List continued on next page.)

FOREIGN PATENT DOCUMENTS

| | | |
|---|---|---|
| 0 179 695 B1 | 4/1986 | European Pat. Off. . |
| 0 346 129 A1 | 12/1989 | European Pat. Off. . |
| 0 346 269 A2 | 12/1989 | European Pat. Off. . |
| 0298235 | 12/1991 | European Pat. Off. . |
| 0 563 332 B1 | 10/1993 | European Pat. Off. . |
| 0 662 309 A1 | 7/1995 | European Pat. Off. . |
| 0 747 025 A1 | 12/1996 | European Pat. Off. . |
| 0 820 740 A1 | 6/1997 | European Pat. Off. . |
| 43 15 757 | 10/1994 | Germany . |
| WO 91/00713 | 1/1991 | WIPO . |
| WO 92/10982 | 7/1992 | WIPO . |
| WO 93/16664 | 9/1993 | WIPO . |
| WO 95/19153 | 7/1995 | WIPO . |
| WO 95/25487 | 9/1995 | WIPO . |
| WO95/31946 | 11/1995 | WIPO . |
| WO 96/11639 | 4/1996 | WIPO . |
| WO 96/11642 | 4/1996 | WIPO . |
| WO 96/40014 | 12/1996 | WIPO . |
| WO 97/20526 | 6/1997 | WIPO . |

OTHER PUBLICATIONS

Susan M. Rapp, Spinal Fusion alternative: Device expands upon implantation, filling disc, Orthopedics Today.

*Primary Examiner*—Mickey Yu
*Assistant Examiner*—Choon P. Koh
*Attorney, Agent, or Firm*—Beyer, Weaver & Thomas, LLP

[57] ABSTRACT

A prosthesis for the replacement of an intervertebral disc of the spine comprises a block of an elastomeric material, which is held under compression by an encapsulating textile fabric. A preferred version of the invention (see FIG. 8) has continuations of the encapsulating fabric forming an interdigitation, with the continuation of the upper fabric passing through a hole in the lower fabric and being attached to the lower vertebral body and the continuation of the lower fabric crossing to its fixation site on the upper vertebral body.

30 Claims, 8 Drawing Sheets

U.S. PATENT DOCUMENTS

| | | |
|---|---|---|
| 5,171,280 | 12/1992 | Baumgartner . |
| 5,171,281 | 12/1992 | Parsons et al. . |
| 5,192,326 | 3/1993 | Bao et al. . |
| 5,246,458 | 9/1993 | Graham . |
| 5,258,043 | 11/1993 | Stone . |
| 5,306,308 | 4/1994 | Gross et al. . |
| 5,306,309 | 4/1994 | Wagner et al. . |
| 5,383,884 | 1/1995 | Summers . |
| 5,401,269 | 3/1995 | Buttner-Janz et al. . |
| 5,458,643 | 10/1995 | Oka et al. . |
| 5,507,816 | 4/1996 | Bullivant . |
| 5,522,898 | 6/1996 | Bao . |
| 5,534,028 | 7/1996 | Bao et al. . |
| 5,534,030 | 7/1996 | Navarro et al. . |
| 5,540,688 | 7/1996 | Navas . |
| 5,545,229 | 8/1996 | Parsons et al. . |
| 5,549,679 | 8/1996 | Kuslich . |
| 5,562,736 | 10/1996 | Ray et al. . |
| 5,562,738 | 10/1996 | Boyd et al. . |
| 5,645,597 | 7/1997 | Krapiva . |
| 5,674,296 | 10/1997 | Bryan et al. . |
| 5,676,702 | 10/1997 | Ratron . |
| 5,683,464 | 11/1997 | Wagner et al. . |
| 5,683,465 | 11/1997 | Shinn et al. . |
| 5,702,450 | 12/1997 | Bisserie . |
| 5,702,454 | 12/1997 | Baumgartner . |
| 5,705,780 | 1/1998 | Bao . |
| 5,716,416 | 2/1998 | Lin . |
| 5,755,796 | 5/1998 | Ibo et al. . |

SURGICAL IMPLANT

This invention relates to surgical implants particularly, but not exclusively, for the replacement of an intervertebral disc of the spine, but also applicable to other indications such as the replacement of a joint within a finger or a toe.

Various forms of disc replacement are in use, although historically, the favoured treatment particularly for a failed cervical disc has been disectomy followed by fusion, using a block or plug of bone inserted into the front of the disc space and abutting into the vertebrae above and below. This bone graft may or may not be stabilised using a plate which is fastened across the front of the disc space. Although fusion may relieve the symptoms for which the surgery was indicated, the loss in mobility of the particular spinal segment is undesirable, particularly in the cervical spine. The fusion of the disc segment also results in hypermobility of the motion segments above and below the fusion with increased strain on the adjacent discs, which can result in their accelerated degeneration, which will in turn require surgical intervention. Fusion using bone graft will have associated donor site morbidity if the bone is autograft or associated risks of infection if the bone is allograft.

Alternatively, following the disectomy the disc space may be left empty, but this leads to hypermobility problems at the operative level, kyphosis, spontaneous fusion and a loss in foraminal height.

Disc prostheses based on either articulating metal plates or metal end plates supporting a polyethylene spacer are in clinical use. Articulating devices reduce the loss in spinal mobility and the degeneration of adjacent discs. However, positioning of the articulating disc prosthesis is critical, with complete failure resulting from even a small error in positioning. The articulation also tends to be non-viscoelastic, uses a fixed axis of rotation, is under constrained in axial rotation and distraction and is therefore unphysiological, not entirely emulating normal motion. As well as the general geometry mismatch, such prosthesis can also be adversely affected by the ingrowth of scar tissue. The long term effect of wear from the articulating surfaces may also be detrimental and there is a high risk of the device being pushed out of the disc space as a result of the failure to precisely match the physiological motion of the spine.

The object of this invention is to provide an artificial disc that attempts to recreate the physiological movement of the spine and also to provide the means to secure the artificial disc in situ both immediately post-operatively and in the long term.

According to a first aspect of the invention we provide a prosthesis, the prosthesis comprising an element of elastomeric or visco-elastic material, the element being provided in a retaining fabric.

The element of elastomeric or visco-elastic material should be thought of as a block, core of insert.

The fabric may constrain the element. The fabric may be discontinuous, for instance provided with apertures or gaps in the fabric. The fabric may engage two or more opposing faces and/or two or more opposing edges and/or two or more opposing corners of the element to restrain it. Engagement with the rear, front and side faces is preferred. Ideally engagement with the top and bottom face may also be provided. Full enclosure of the element by the fabric represents a preferred form of the invention.

According to a second aspect of the invention, the disc prosthesis comprises a block of an elastomeric or viscoelastic material which is encapsulated by a textile fabric.

The block could equally well be referred to as a core or insert provided within the textile fabric of the prosthesis. Block, core and insert and used in an interchangeable manner in this document.

Preferably the block is formed of silicon rubber. Preferably the block has a Shore A scale hardness of 35 to 80°.

The block is preferably formed of a biocompatible material. The block may be formed of a reabsorbable material.

Preferably the block provides substantially equivalent properties and/or behaviour to the nucleus pulposis of a natural disc, for instance during compression and/or distraction and/or horizontal gliding and/or axial rotation and/or flexion and/or extension.

The block may be provided with a flat upper surface and/or a flat lower surface. The block may be provided with upper and/or lower surfaces that are curved in a convex manner. The maximum thickness of such blocks may be centrally provided. The provision of both planar upper and/or lower surfaces is preferred. The area of the upper surface is preferably greater than the area of the lower surface. The maximum width of the upper surface is preferably greater than the maximum width of the lower surface. The minimum width of the upper surface is preferably greater than the minimum width of the lower surface.

The block may be provided with sides extending between the upper and lower surfaces. The sides may be planar or curved, most preferably curved in a convex manner.

Although the front thickness of the block may be less than the back thickness of the block, preferably the front thickness of the block is more than the back thickness of the block. The front being the portion of the block nearer the front of the spine in use. The thickness of the front and back of the block may be equal and less than the thickness at a point partway, for instance midway, between the front and the back of the block.

The block may be wider towards the rear face than towards the front face, but the block is preferably wider towards the front face than towards the rear face. The width may decrease in a linear manner from in proximity to the front face to in proximity to the rear face of the block.

The interface between the sides and top and/or bottom surfaces may be curved. The interface between the sides and front and/or rear faces of the block may be curved. The interface between the front and/or rear face and the top and/or bottom faces may be curved.

Preferably the maximum length, l, from the front face of the block to the rear face of the block is between 8 and 18 mm and more preferably between 10 and 15 mm. Preferably the maximum width of the upper surface is between 10 and 18 mm, and more preferably between 12.5 and 16.5 mm. Preferably the minimum upper width is between 8 and 15 mm and more preferably between 9.5 and 13.5 mm. Preferably the maximum lower width is between 9 and 16 mm, and more preferably between 10.5 and 14.5 mm. Preferably the minimum lower width is between 7.5 and 13.5 mm and more preferably between 8.5 and 12.5 mm.

Preferably the maximum thickness of the block is between 2 and 6 mm, and more preferably between 2.5 and 5.5 mm. Preferably the minimum thickness of the block is between 1.25 and 4.75 mm and more preferably between 1.75 and 4.25 mm.

The block may be provided according to any four dimensions, more preferably any five, or any six, or any seven, or eight, or nine dimensions of any one of the blocks provided in Table 1 included herein, the dimensions including dimension sizes +/− 0.25 mm on the values listed.

A particularly preferred form of the block provides planar upper and lower surfaces, the upper surface having a greater width than the lower surface, the block having a greater thickness towards the front face than towards the rear face. The front face may be planar and/or the rear face may be curved.

In one embodiment of the invention, the encapsulated disc prosthesis is preferably a rectangular block (although it may have a circular or oval cross-section). Typical dimensions for a disc prosthesis for the cervical spine would be 13 mm wide by 12 mm deep by 4 mm in height.

The fabric may be made of polyester or any other suitably strong flexible and biocompatible material. The fabric may be formed of, or comprise, materials including polyester, polypropylene, polyethylene, carbon fibre, glass, glass fibre, polyaramide, metal, copolymers, polylactic acid, polyglycolic acid, biodegradable fibres, silk, cellulosic and polycaprolactone, including mixtures of one or more of these materials and including fibres made therefrom.

The textile fabric may be formed using weaving, knitting, braiding or embroidery.

The fabric may be produced in the desired profile or may be reduced to the desired profile from a larger amount of fabric, for instance by cutting or pressing. The fabric may be or may also be made of a resorbable material.

The structure and/or properties of the fabric may be selected to encourage tissue ingrowth.

The fabric component may be formed from a planar fabric element. The fabric component may be formed from a piece of fabric having a first portion and a second portion, the first and second portions being joined by an integral part of the fabric or by an attaching technique, such as stitching. Preferably the first and second portions are folded, or otherwise provided in opposition to one another, to give the block encapsulating portion of the fabric component. The edges of the first and second portions may be stitched or otherwise attached to one another to provide the encapsulating portion of the fabric component. A pocket, open at one end, may be formed in this way.

The fabric component may be provided with one or more further portions, preferably attached to the first and/or second portion, to provide closure for the pocket receiving the block.

A single further portion, extending across the opening may be provided.

The first further portion attached to the first portion and a second further portion attached to the second portion may be provided, the first and second further portions being attached to one another to provide closure for the pocket.

The first and second further portions may extend from the first and second portions, for instance to form flanges. These further portions/flanges may be attached to the vertebrae adjacent to the prosthesis in use. In such cases the first further portion may be attached to the vertebrae adjacent the first portion of the encapsulating material and the second further portion may, additionally or alternatively, be attached to the vertebrae adjacent the second portion of the encapsulating material.

In a preferred embodiment of the invention, one of the first or second further portions is provided with an aperture. The other further portion may be provided with a reduced dimension neck in such instances. Preferably the first and second further portions are interdigitated in the assembled form. Interdigitation may be affected by passing one of the further portions through the aperture in the other further portion. The first further portion may be attached to the vertebrae adjacent the second portion of the encapsulating material and/or the second further portion may be attached to the vertebrae adjacent the first portion of the encapsulating fabric.

The gap between the vertebrae may be spanned by a separate fabric element from the prosthesis and attached to the vertebrae adjacent the prosthesis. This element may provide closure of the prosthesis. In an alternative form the element may be provided as a continuation of the first or second further portions of the prosthesis fabric material.

The first and/or second further portions and/or the separate element may be provided with apertures to receive anchors.

Anchors such as bone screws, staples or the like may be employed.

In a particularly preferred form of the invention a portion of one of the further portions passes through an aperture or gap in the other further portion, and an element is provided within the pocket between the block and the location where the one further portion passes through the other. The element is preferably a pad or cushion of resilient but deformable material, for instance the fabric used for the encapsulating fabric. The element may be discrete from the encapsulating fabric. It is preferred, however, that the element be formed of the fabric material and that it be integral with the encapsulating fabric material. The element may be formed by folding a portion of the fabric material. Multiple folds may be used to form the element. The fabric forming the element may be provided on one or both of the further portions and/or on one or both of the portions of the fabric material and/or at the junction between a portion and its further portion. Preferably the block is constrained and/or retained by the fabric, but is not attached to the fabric.

Encapsulation may be provided by fully enclosing the block within the fabric. Encapsulation may be provided by providing the block within a fabric constraint. The fabric constraint, may for instance, engage some or all of the corners and/or some or all of the edges of the block, but be absent from one or more portions of the faces.

The encapsulation of the elastomeric block may be by insertion of a solid block or injection of a liquid into a textile receptacle. The textile receptacle may be formed by stitching or sealing closed the ends of a tubular fabric or by folding a fabric onto itself and stitching or sealing closed the free edges.

Preferably the fabric compresses the block.

Preferably one or more prostheses as herein defined provide a complete disc replacement, most preferably in the cervical portion of the spine.

Preferably, a single disc prosthesis, comprising for instance an elastomeric block held under compression by an encapsulating textile fabric, is inserted into the disc space from the front of the spine. Alternatively, a pair of disc prostheses may be inserted into the disc space from the back of the spine.

Preferably the prosthesis is between two adjacent vertebrae, with the front edge of the textile fabric being level with the front edge of the vertebrae and the elastomeric block recessed relative to the front edge of the vertebrae. Recessing of the block by between 1 and 4 mm is preferred.

Preferably the block component of the prosthesis acts as a replacement for the nucleus pulposis, the fabric provides a replacement for the annulus, and optionally, the flange elements provide a replacement for the anterior longitudinal ligament which is the ligament extending along that portion of the spine.

According to a third aspect of the invention we provide a method of producing a disc prosthesis, the method comprising providing a block of an elastomeric or visco-elastic material and forming an encapsulating textile fabric component, the block being placed within the fabric component.

According to a fourth aspect of the invention we provide a set of two or more prosthesis according to the first aspect of the invention and incorporating blocks of different sizes.

According to a fifth aspect of the invention we provide a surgical technique for providing a disc prosthesis, the technique comprising removing the natural disc and replacing the disc with a prosthesis according to the first aspect of the invention.

The third, fourth and fifth aspects of the invention may include any of the details, options and possibilities set out elsewhere in the application.

The invention, and its use, will now be described, by way of example, with reference to the accompanying drawings, in which:

FIG. 3b illustrates a maximum cross section of the block of FIG. 3a;

FIG. 3c illustrates a minimum cross section of the block of FIG. 3a;

FIG. 3d illustrates a side view of the block of FIG. 3a;

FIG. 3e illustrates a side view of an alternative embodiment of the block of FIG. 3a;

Figure 1:
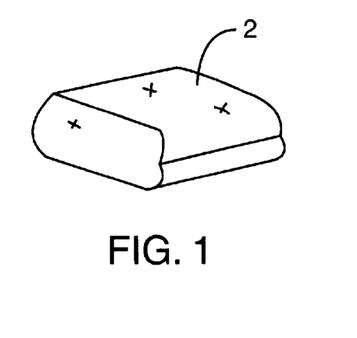
FIG. 1 is a view of the basic prosthetic disc with a textile fabric encapsulating a block of viscoelastic rubber.

In FIG. 1, an elastomeric rubber block such as silastic, is encapsulated and held in compression by a textile fabric 2.

The elastomeric block may be a silicone rubber, for instance with a Shore A scale hardness of 35–80°.

The fabric used in the invention may be formed by flat or circular weaving, knitting, braiding or preferably embroidery. A wide variety of fibre materials are applicable to the fabric, including, polyester, polypropylene, polyethylene, carbon fibre, glass, glass fibre, polyaramide, metal, copolymers, polylactic acid, polyglycolic acid, biodegradable fibres, silk, cellulosic and polycaprolactone fibres.

The structure of the fabric is selected such that fibrous tissue may penetrate between the fibres or threads forming the fabric. Tissue ingrowth is highly desirable and may even be possible to an extent where in growth replaces one or more components of the prosthesis. Biodegradation of the prosthesis may be encouraged in such cases, for instance giving rise to replacement of the fabric and/or even disc regrowth.

Figure 2:
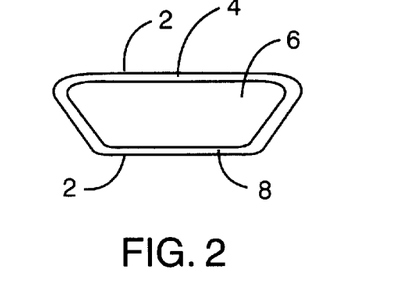
FIG. 2 is a view of the preferred cross-section in the frontal plane for a cervical disc.

In FIG. 2, the cross section has been modified to match that of the natural cervical disc with the upper surface 4 of the disc 6 having a larger surface area than the lower surface 8 of the disc. The textile fabric 2 conforms to the profile of the disc 6.

To render the prosthesis suitable for use in replacing the different discs of the spine (with their consequential variation in size) and to render the prosthesis suitable for treating a variety of patient sizes (with consequential variation in the size of the discs to be replaced) the core for the prosthesis is provided in a variety of sizes.

As illustrated in FIGS. 3a, 3b, 3c and 3d a variety of dimensions are of relevance in detailing the size of prosthesis core provided.

Figure 3A:
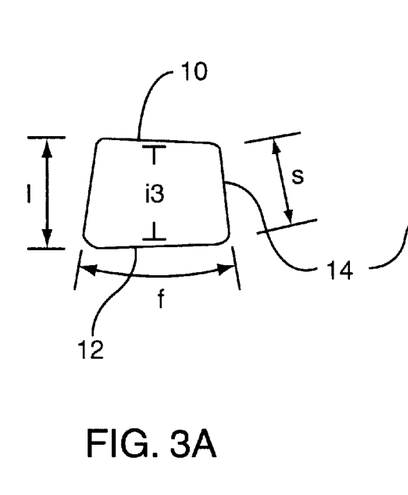
FIG. 3a illustrates a top plan view of a block for use in a spinal prosthesis.

In FIG. 3a the maximum length, l, from the front face 10 of the disc to the rear face 12 of the disc is illustrated, together with the actual length, s, of the inclined side 14 connecting the front face 10 of the core to the junction with the rear face 12 of the core. The length of the rear face, f, between the junction with the first side 14 and second side 14 is also illustrated.

Figure 3B:
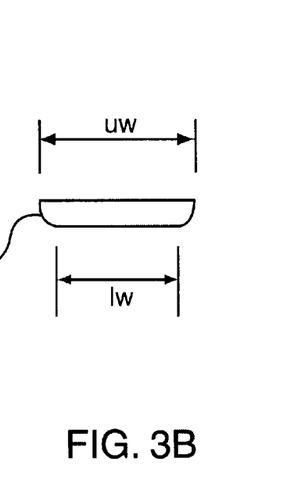

FIG. 3b illustrates the maximum cross section of the core, normally taken parallel to front face 10, and generally the cross section extending between one rear face 12 to side 14 junction and the other rear face 12 to side 14 junction. The cross section illustrates the maximum upper width, uw, and the maximum lower width, lw.

Figure 3C:
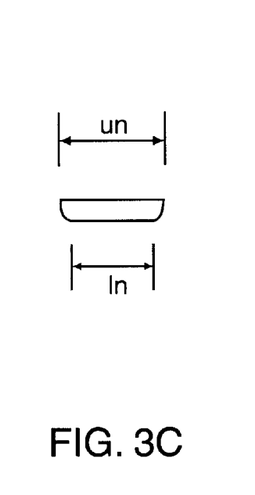

The FIG. 3c illustration displays the minimum width cross section, generally provided at or in proximity to the front face 10. This Figure illustrates the minimal upper width, un, and the lower minimal width, ln.

Figure 3D:
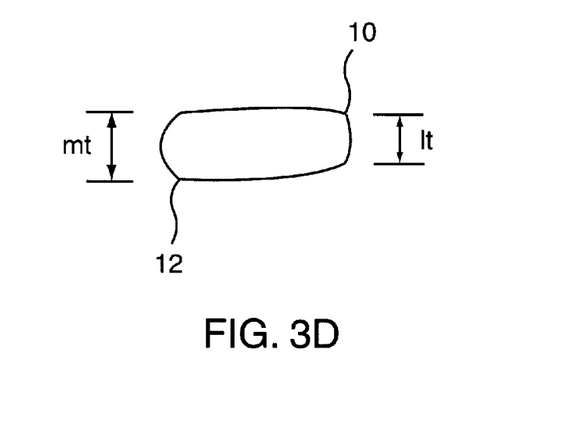
Figure 3E:
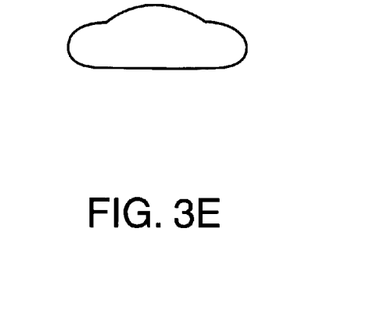

FIG. 3d illustrates, from the side, the variation in thickness of the core between the front face 10 and the rear face 12. The maximum thickness, mt, is generally provided at or in proximity to the rear face 12, with the lowest thickness, lt, generally being provided at or in proximity to the front face 10.

The corners of the core are generally rounded, as illustrated.

Typical sizes for the dimensions described above may be provided according to the following table.

| Max upper width (uw) | Max lower width (lw) | Min upper width (un) | Min lower width (ln) | Max thickness (mt) | Min thickness (lt) | Max length (l) | Max side length (s) | Rear face length (f) |
|---|---|---|---|---|---|---|---|---|
| 14 | 12 | 11 | 10 | 4 | 3 | 13 | 12 | 14 |
| 14 | 12 | 11 | 10 | 3.5 | 2.5 | 12 | 11 | 14 |
| 14 | 12 | 11 | 10 | 3 | 2 | 11 | 10 | 14 |
| 13 | 11 | 10 | 9 | 3.5 | 2.5 | 13 |  | 13 |
| 13 | 11 | 10 | 9 | 3 | 2 | 12 |  | 13 |
| 13 | 11 | 10 | 9 | 3 | 2 | 11 |  | 13 |
| 16 | 14 | 13 | 12 | 5 | 4 | 14 | 13 | 16 |
| 16 | 14 | 13 | 12 | 4 | 3 | 13 | 12 | 16 |
| 16 | 14 | 13 | 12 | 3 | 2 | 12 | 11 | 16 |
| 15 | 13 | 12 | 11 | 4 | 3 | 13 | 12 | 15 |
| 15 | 13 | 12 | 11 | 3.5 | 2.5 | 12 | 11 | 15 |
| 15 | 13 | 12 | 11 | 3 | 2 | 11 | 10 | 15 |

Sets of prostheses of different sizes may be offered for a particular disc in the spine. The correct size may be evaluated by inserting into the vacant disc space metal sizers, each provided on a rod, and of each corresponding in its dimensions to the profile of a prosthesis.

Figure 4:
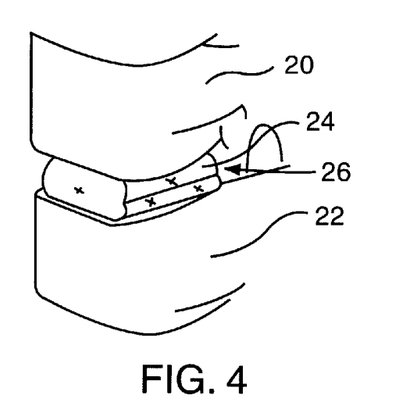
FIG. 4 is a view of the basic prosthetic disc in situ between adjacent spinal vertebrae.

FIG. 4 is a perspective view from the front of a spine of two adjacent vertebral bodies 20, 22 with the prosthetic disc 24 in the disc space 26 between them.

Prosthesis of the type provided in the present invention are inserted following a disectomy. This involves removing the portion of the anterior longitudinal ligament spanning the vertebral space in question, removing the disc (both annulus and nucleus pulposis) and inserting into the vacant disc space the prosthesis. Where applicable, the prosthesis is then anchored in place, as described in more detail below. The front edge of the solid core is positioned level with, or more preferably recessed relative to the front edge of the vertebrae, for instance by 2 to 4 mm.

This technique is surgically attractive in that the preparation of the disc space, to receive the disc prosthesis, involves steps already established for standard disc removal surgery. The surgeon is thus not required to change techniques.

Figure 5:
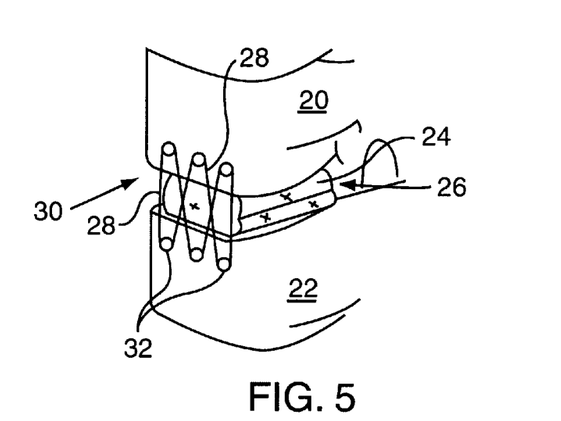
FIG. 5 is a similar view to FIG. 4 for a further embodiment of the invention with the addition of a "cat's cradle" of suture threads which acts to secure the disc prosthesis in situ within the disc space and which contributes to the stability of the disc reconstruction by replacing the anterior annulus, which is the fibrous structure across the front of the disc space.

In FIG. 5, an equivalent disc prosthesis 24 to that employed in FIG. 4 is provided, together with a "cat's cradle" construction 28 added to the front 30 of the spine.

The construction 28 is anchored to the vertebral bodies 20, 22 on either side of the disc space 26 using fixation devices 32 imbedded into the vertebrae and defining the apex of each element of the cradle. Alternatively the cradle 28 may be formed by passing the elements of the cradle, such as a suture around the head of a screw secured to the vertebral body to define the apex of each cradle element.

Other fixings, such as staples, may be used in this and other embodiments of the present invention.

This construction 28 may be formed of either single or multiple yarns, sutures, braids or other flexible textile elements which are formed into a loop either before or during the operation.

The cradle 28 acts to secure the prosthetic disc 24 within the disc space 26 while the spine is being flexed, extended or rotated. The cradle 28 also acts to support the motion segment of the spine by providing textile fibres that match the orientation of the fibres within the natural annulus, which is the fibrous structure across the front of the disc space.

The construct or cradle 28 may be added to any of the applications shown in FIGS. 6 to 9.

Figure 6:
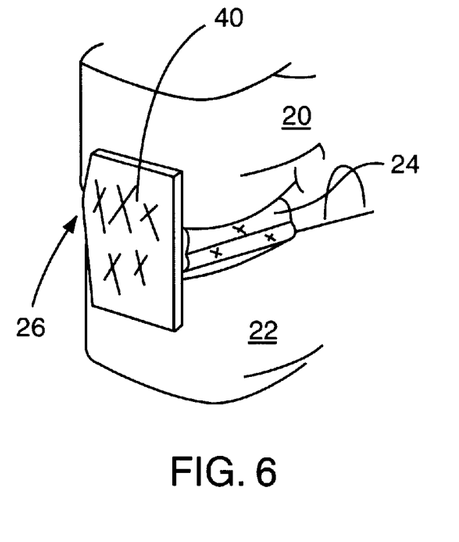
FIG. 6 is a similar view to FIG. 4 for a further embodiment of the invention but with the "cat's cradle" replaced with a textile fabric which may be either a separate textile fabric placed across the opening of the disc space or a textile fabric that is attached to the disc prosthesis

FIG. 6 shows the cradle replaced with a preformed fabric element 40, which may have fibres arranged within it which match the orientation of the cradle structure detailed above. This fabric element 40 may be either a separate element positioned across the front of the disc space 26 after the insertion of the prosthetic disc 24, as shown, or it may be attached to the disc 24. The element 40 may be secured to the vertebral bodies 20, 22 on either side of the disc space 26 by sutures passing to bone anchors (not shown) implanted into the vertebrae. Alternatively, the fabric element 40 may be secured using bone screws (not shown) passing either directly through the fabric element 40 or inserted through fixation holes in the fabric, with or without the use of a reinforcing element, such as a washer or rivet. Alternatively the fabric element 40 may be secured by a pair of metal plates (not shown), one of which is fastened to each vertebral body 20, 22 over the fabric element 40.

Figure 7:
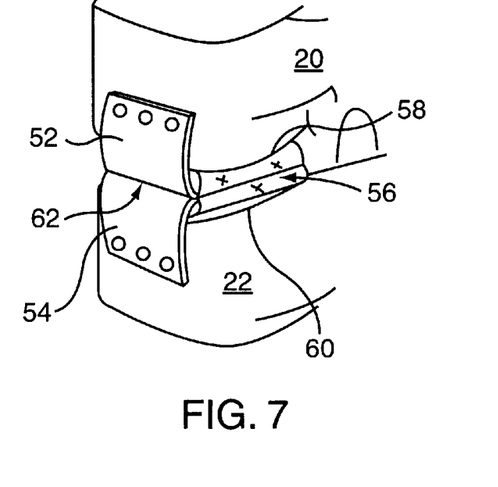
FIG. 7 is a similar view to FIG. 6 for a further embodiment of the invention but with the element of the invention across the front of the disc space created from a continuation of the encapsulating fabric.

In FIG. 7, the fabric forming the flanges 52, 54, each for attachment to a vertebral body 20, 22, is a continuation of the encapsulating fabric 56. The fabric 56 on the upper surface 58 of the prosthetic disc passing to the front of the upper vertebral body 20 and the fabric 56 on the lower surface 60 of the prosthetic disc passing to the front of the lower vertebral body 22. The elastomeric block within the fabric 56 is held in position by the upper 52 and lower 54 fabric elements being fastened to each other in a line 62 along the front edge of the prosthetic disc.

Figure 8:
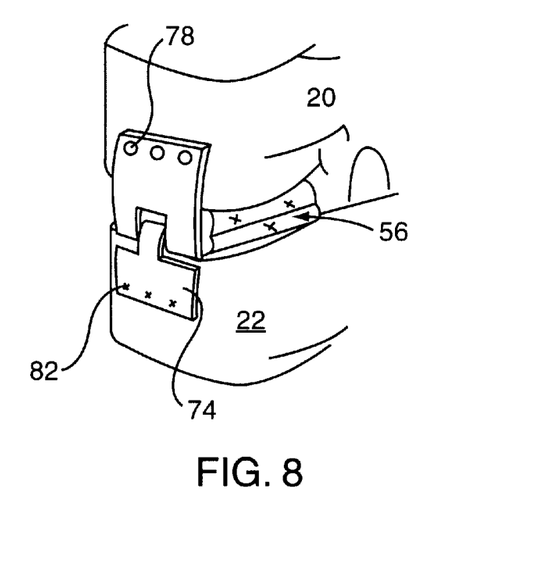
FIG. 8 is a similar view to FIG. 7 for a further embodiment of the invention but with the continuation of the encapsulating fabric forming an interdigitation with the continuation of the upper fabric passing through a hole in the lower fabric and being attached to the lower vertebral body and the continuation of the lower fabric crossing to its fixation site on the upper vertebral body.
Figure 9:
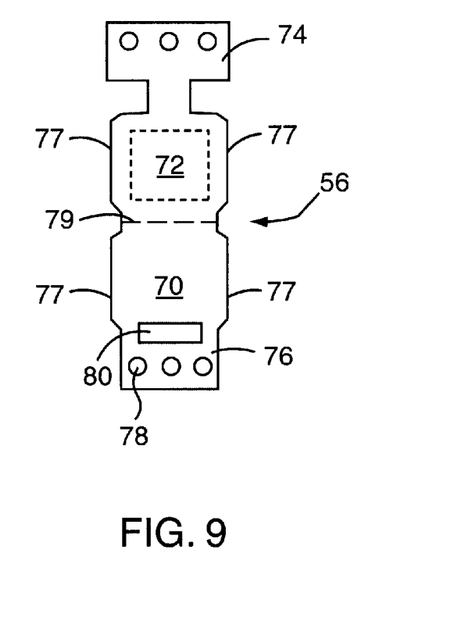
FIG. 9 is a plan view of the fabric profile used in the FIG. 8 embodiment of the invention.

FIG. 8 a shows a preferred version of the invention in its position of use. FIG. 9 illustrates the plan profile of the textile element of the construction shown in FIG. 8 before the sides of the encapsulating element have been fastened together. The view shows the inside surfaces of the lower face 70 and upper face 72 of the encapsulating fabric, the faces 70, 72 facing one another in the assembled form, the core being provided between these two faces. The continuations 74, 76 of the encapsulating fabric 56 form an interdigitation in the assembled state.

To assemble the fabric, faces 70, 72 are sewn together along edges 77 to form a pocket sealed at the edges 77 by the stitches and at the back by the junction 79 of the two faces 70, 72. The continuation 74 of the upper fabric 72 is passed through a hole 80 in the continuation of the lower fabric 76 and is attached to the lower vertebral body 22. The continuation 76 of the lower fabric crosses over to its fixation site on the upper vertebral body 20 as a result.

For the purposes of illustration, the flange 76 attached to the upper vertebral body 20 is secured using bone screws (not shown) received in apertures 78 in the flange 76 and the flange 74 attached to the lower vertebral body 22 is attached using sutures 82 which are in turn attached to bone anchors (not shown) imbedded in the vertebral body.

The tension on the flanges created by the extension of the spine will tend to pull the disc element even more securely back within the disc space. This is contrary to some prior art prosthesis in which particularly extension of the spine can tend to promote the ejection of the disc element out of the disc space.

The visco-elastic properties of the prosthetic disc are an ideal match of the visco-elastic properties of the natural disc when the encapsulated textile/elastomeric inserts are subjected to compression/relaxation with the constructs illustrated in FIGS. 8 and 9. Flexion of the spine will impose a direct compressive load on the prosthetic disc and extension of the spine will create tension in the flanges 74, 76 which will by virtue of the interdigitation impose a compressive load on the prosthetic disc.

Many of the benefits of the present invention stem from the manner in which the properties of the prosthesis directly correspond to features of the natural disc replaced. The prosthesis in effect mimics a natural disc to a large extent. The deformable core, insert or block performs a very similar function to the nucleus pulposis. The fabric encapsulation performs a very similar function to the annulus. The flanges perform a very similar function to the anterior longitundinal ligament extending down the front of the spine.

The pattern of FIG. 9 may be cut out of a preformed fabric but it is preferably formed using embroidery which can optimally position the fibres within the fabric to maximise the load bearing potential of the construction.

Figure 10:
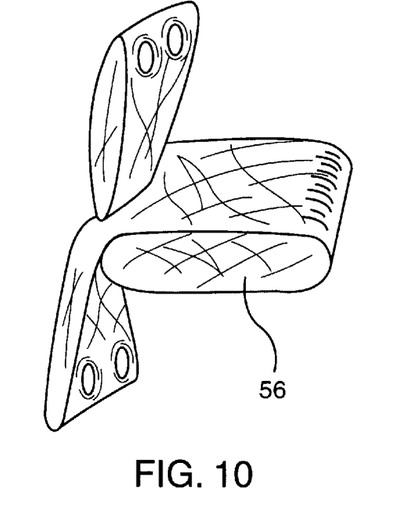
FIGS. 10 and 11 are perspective views of a modified version of the embodiment of the invention illustrated in FIG. 8.
Figure 11:
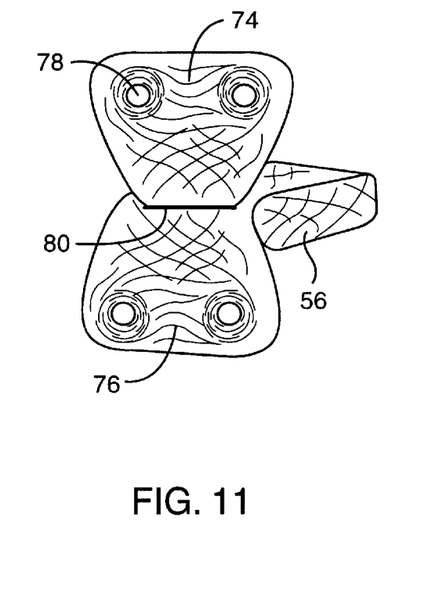

FIGS. 10 and 11 are further illustrations of the embodiment of the invention illustrated in FIGS. 8 and 9. The prosthesis comprises a fabric sheath for an internal core of resilient but suitably deformable material. Flanges 74, 76 extend from the sheath 56 and are interdigitated, in the manner outlined above, by passing the flange 74 through the aperture 80 in the flange 76. In the illustration the flanges 74, 76 each taper outward from a reduced width where they interdigitate to an increased width towards the anchor receiving apertures 78.

Figure 12:
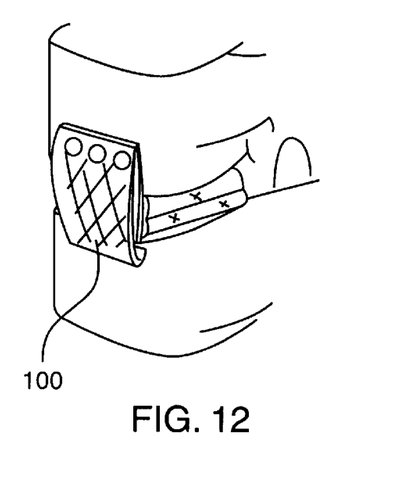
FIG. 12 is a similar view to FIG. 6 for a further embodiment of the invention but with additional fabric across the front of the device which may either be a separate fabric or a continuation of the encapsulating fabric.

In FIG. 12, the type of construction shown in FIG. 8 has an additional fabric element 100 added over the front of the device, in a manner similar to that shown in FIG. 6. This element 100 may be either a continuation of the upper 76 or, as shown, lower 74 flange, or a separate fabric element. The additional fabric element 100 acts to increase the torsional resistance of the construction. It limits the compression of the silicon insert resulting from the tension in the flanges when the spine is placed in extension and it also is a barrier to prevent the backing-out of bone screws used to secure the flanges to the vertebral bodies 20, 22.

Figure 13:
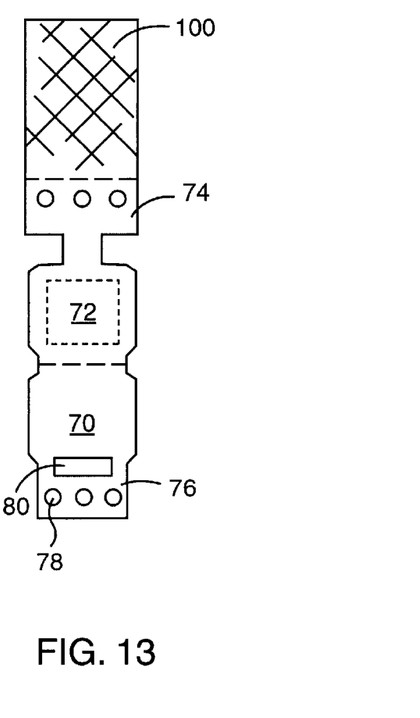
FIG. 13 is a plan view of the fabric profile used in the FIG. 12 embodiment of the invention.

FIG. 13 shows a similar plan view to that shown in FIG. 9 but with the addition of the fabric 100 to be attached over the front of the construction when in situ.

Figure 14:
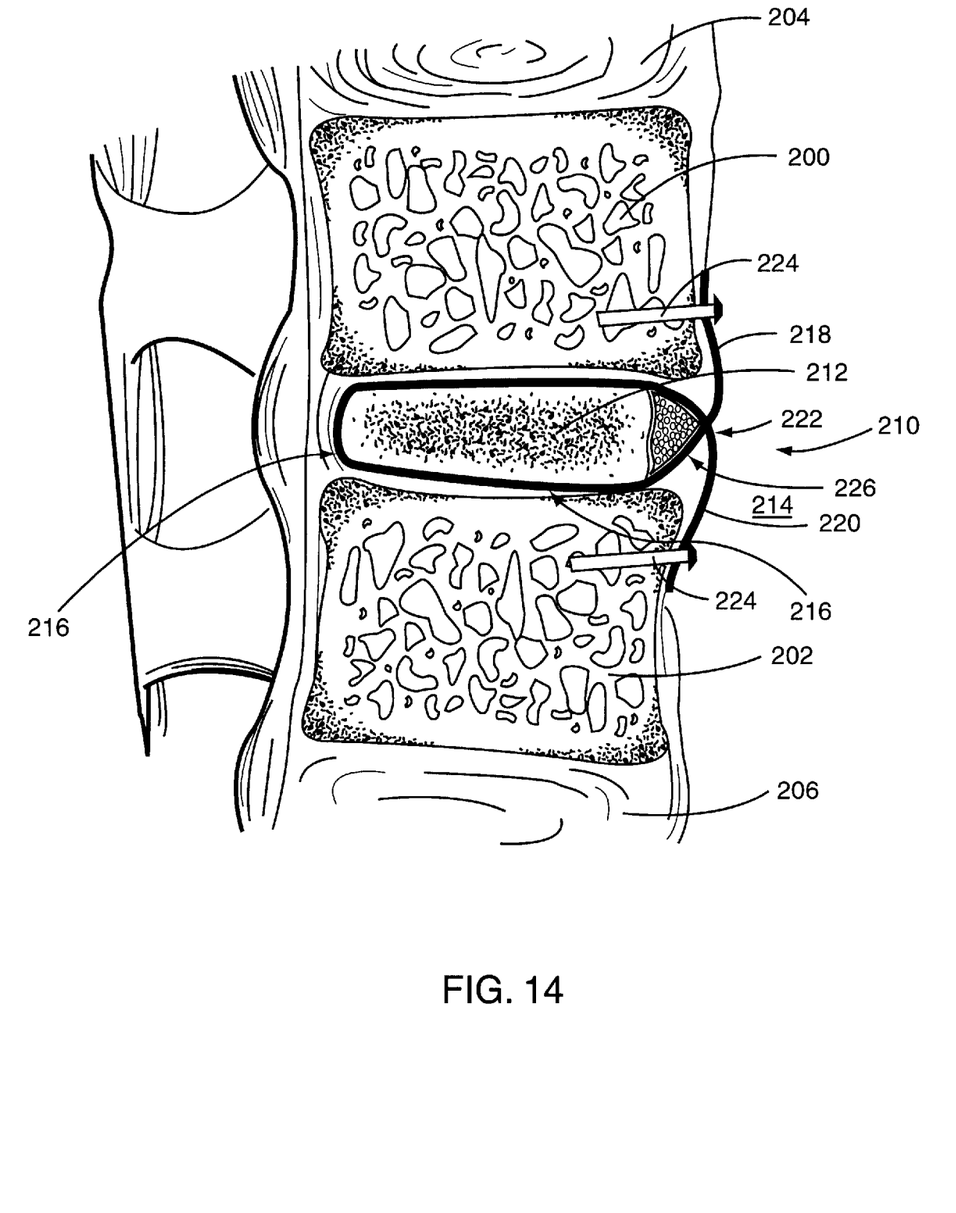
FIG. 14 illustrates the prosthesis of FIGS. 12 and 13 in situ in a spine, in cross section.

The prosthesis 210, FIG. 14, replaces the natural disc between vertebrae 200 and 202.

As illustrated, the prosthesis 210 is provided according to the form illustrated in FIGS. 10 and 11 and comprises a visco-elastic block, insert or core 212, of greater thickness near the insertion side 214 than away from the insertion side 214. This conforms to the natural shape of the space between the vertebrae 200 and 202. The insert 212 is encased in the fabric 216 in the manner described above. The flanges 218 and 220 extending from the disc space are interdigitated at location 222 and fixed by bone anchors 224. The prosthesis is provided with a fabric pad 226 between the interdigitation location 222 and the core 212. This promotes the correct positioning of the core 212 relative to the vertebrae and the overall prosthesis when the spine is in both flexion and extension. By providing the pad 226 this extension of the spine tends to pull the flanges 218, 220 apart and so squeeze the pad 226 towards the interior of the disc space holding the insert 212 in position.

When the spine is in flexion, the pad 226 holds the insert 212 away from the front of the disc space where the compression force exerted by the vertebrae 200 and 202 is greatest.

Figure 15:
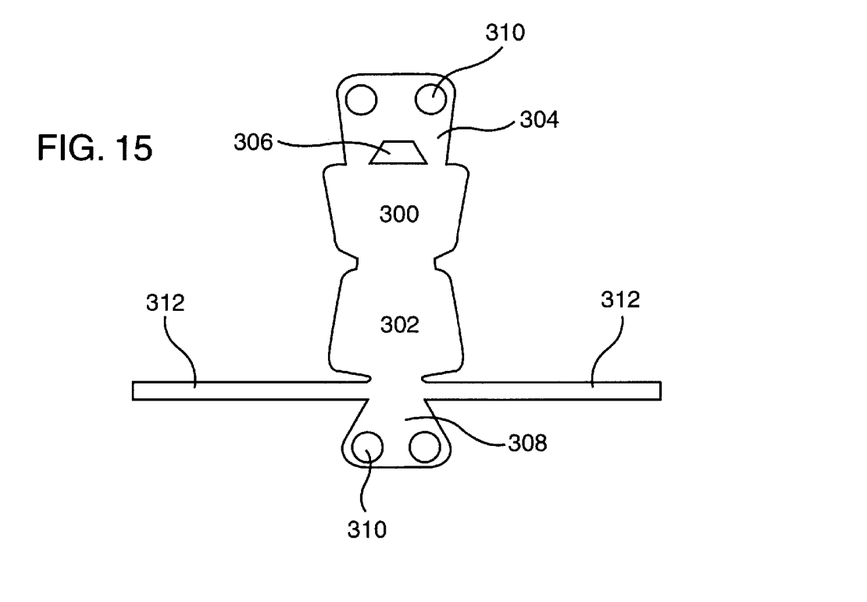
FIG. 15 illustrates a plan view of the fabric profile of a further embodiment of the invention.
Figure 16:
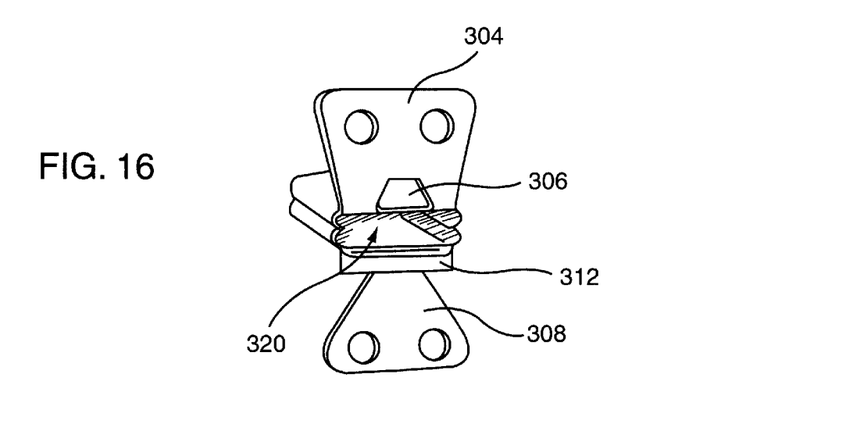
FIG. 16 illustrates the fabric profile of FIG. 15 in a part assembled state, prior to insertion of the core.
Figure 17:
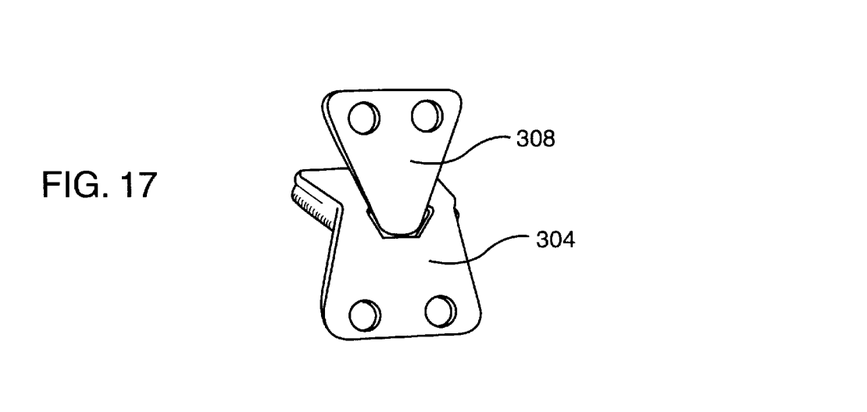
FIG. 17 illustrates the embodiment of FIG. 16 in a final assembled form.

The pad 226 may be provided as a distinct element, as shown, which is introduced during assembly, or more preferably, the type of construction illustrated in FIGS. 15, 16 and 17 may be provided.

FIG. 15 represents in plan view the fabric component prior to assembly. Faces 300 and 302 face one another and contact the core in use. Flange 304 is provided with an aperture 306 through which the opposing flange 308 is interdigitated in use. Apertures 310 are provided in the flanges 304, 308 to accommodate the anchors.

This embodiment of the invention also includes laterally extending arm portions 312 made of the fabric material. These arm portions are folded into multiple folds, in use, to provide the cushion pad between the interdigitation location and the core.

FIG. 16 illustrates the fabric encapsulation of FIG. 15 in its assembled state prior to the insertion of the core. The arms 312 are folded in on one another to provide a cushion mounted on the lower flange 308. Once assembled in this configuration the core, not shown, is inserted into the internal space 320. Following core insertion, the lower flange 308 is passed up through the aperture 306 in the upper flange 304. This pushes the folded pad 312 across the aperture leading to the core and provides a cushion for the core. Once fully interdigitated the structure resumes the format illustrated in FIG. 17.

In use the pad 312 provides the benefits outlined above in relation to FIG. 14 by promoting retention of the core within the disc space. The pad provides complete encapsulation of the core and also ensures that the edge of the core is held back from the front edge of the disc space. This hold back is beneficial in ensuring that no block to the full flexion of the vertebrae adjacent to the disc space. The risk of the front edge of the prosthesis being nipped by the front edge of the disc is also reduced.

The prosthesis structures provided according to the present invention enable a more natural movement to be provided in spines where disc damage would normally necessitate fusion and no mobility at that location or the provision of a vacant disc space and hypermobility at that location. The prosthesis is closely matched to a natural disc in terms of disc height, stiffness in compression and three planes of rotation, viscoelastic behaviour and the transmission of physiological stress to adjacent vertebrae.

Prostheses of the present invention are also beneficial over those used in the prior art in terms of their ease of positioning, tolerance in positioning and in terms of the physiological nature and extent of the movement provided. Behaviour more closely replicating natural discs is provided.

It is a particularly important benefit of the present invention that the effects of introducing a prosthesis according to the invention on the adjacent motion segment of the spine are far less pronounced. Problems with increasing the rate of damage or problem formation in the adjacent discs are thus avoided too.

Whilst allowing physiological axial rotation, horizontal gliding and vertical distraction the structure of the prosthesis provides suitable constraints to excessive movement.

These benefits are provided with a prosthesis formed of materials which have proven biocompatibility in other applications, sufficient mechanical endurance and avoid wear particle formation.

Whole cervical spine and single motion segment cadaveric testing have confirmed the more natural movement achieved, both in the spine as a whole and in the individual joint. Fatigue testing over a million cycles indicated no damage to the fibre encapsulation or to the insert itself.

Figure 18:
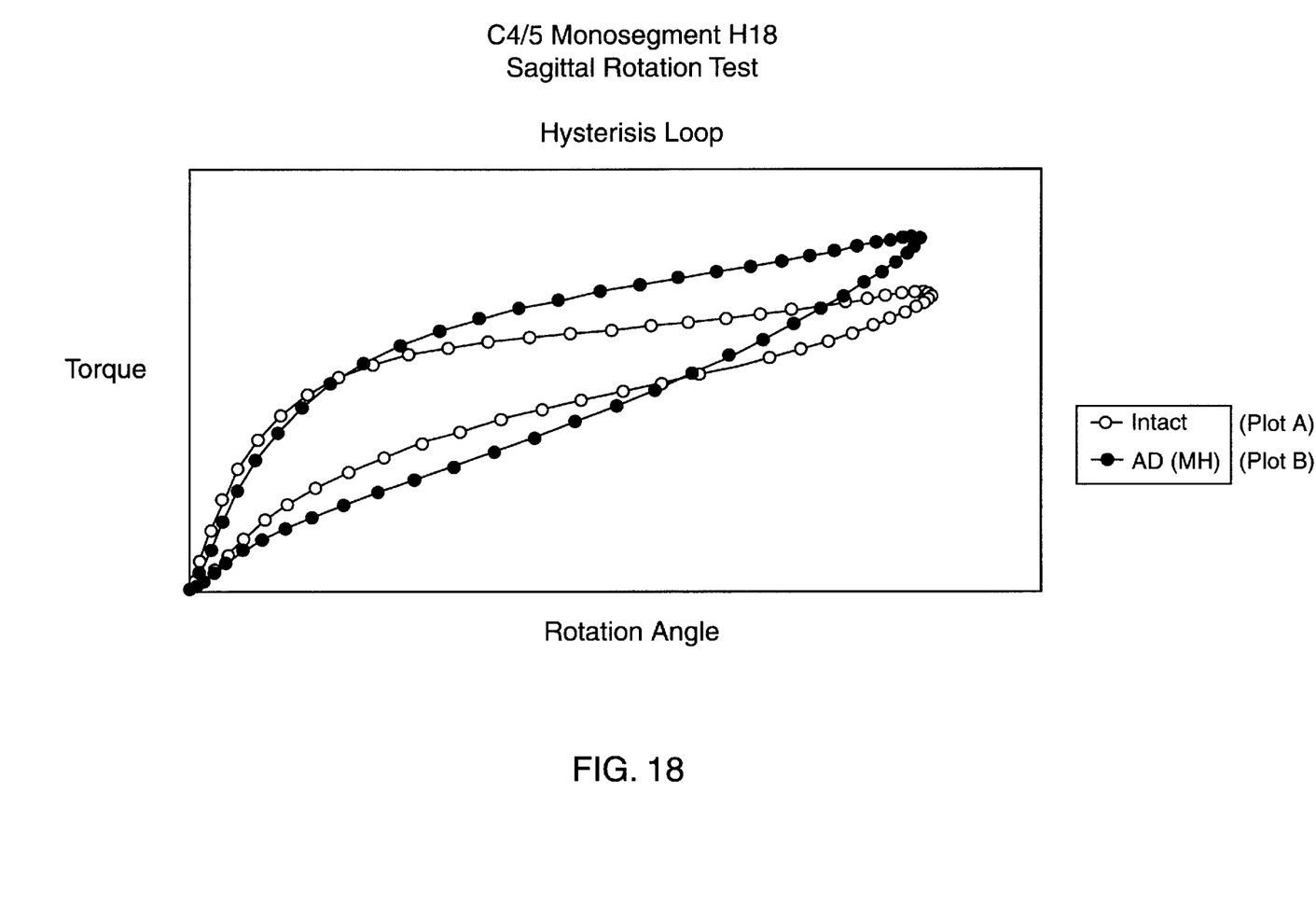
FIG. 18 illustrates the torque against rotational angle results for a sagittal rotation test on a monosegment C4/5.

FIG. 18 illustrates the hysteresis loop for sagittal rotation of a C4/C5 joint with a natural disc, plot A, (the arrows indicate the direction of flexure, left to right for forward, right to left for back) and for a disc according to the present invention, plot B. As can clearly be seen the plots very closely match one another reflecting the near equivalence of the prosthesis to the natural disc during such movement. The deviation between the plots is within the variation arising between two natural discs.

Figure 19:
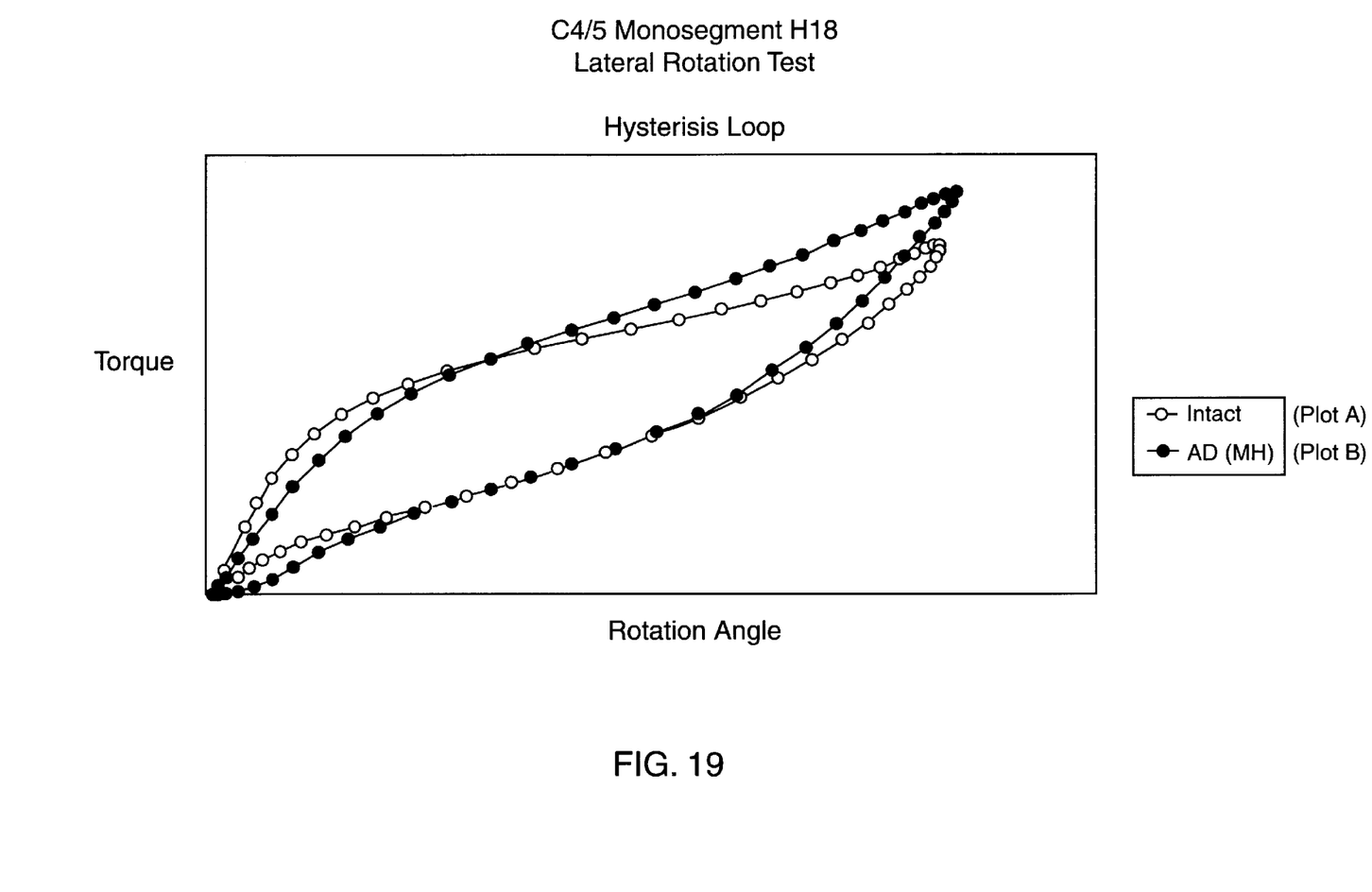
FIG. 19 illustrates the torque versus rotational angle results for a lateral rotational test on a C4/5 monosegment.

FIG. 19 shows a similar set of hysteresis plots for a natural disc, plot A, and a prosthesis according to the invention, plot B, during a lateral rotation test, again illustrating the near equivalence in performance.

Multi-segment evaluation of the prosthesis also indicated that the position of the centre of rotation was very similar when a prosthesis according to the present invention was deployed, when compared with a fully natural disc multi-segment test.

Similarly the % contribution to the movement was a far closer match between the present invention's prosthesis and a natural disc, than between any of the prior art prosthesis or surgical techniques and a natural disc multi-segment.

Over and above these advantages, if the prosthesis should fail for some reason, it is far easier to remove to the necessary extent to enable a fusion (the recognised follow up treatment for a failed prosthesis) to be performed. The present invention merely needs the fabric to be cut to an extent enabling the core to be removed. The fabric flanges can be left in-situ, avoiding problems where, for instance, significant tissue in-growth has occurred. Tissue in-growth on the flanges may be avoided by providing an in-growth retarding coating to these parts.

What is claimed is:

1. A disc prosthesis comprising a block of an elastomeric or visco-elastic material which is encapsulated by a textile fabric and in which a flange, suitable for attachment to vertebral bodies, is provided as a fabric continuation of the encapsulating fabric.

2. A prosthesis according to claim 1 in which the elastomeric block is held under compression by the encapsulating textile fabric.

3. A prosthesis according to claim 1 in which the fabric is formed using weaving, knitting, braiding or embroidery.

4. A prosthesis according to claim 1 in which the block is encapsulated by inserting the block into a textile receptacle formed by folding the fabric on to itself and stitching or sealing closed the free edges.

5. A prosthesis according to claim 1, wherein the disc prosthesis has an upper surface and a lower surface and in which the upper surface of the disc has a larger surface area than the lower surface of the disc.

6. A prosthesis according to claim 1 in which the prosthesis is provided with an upper fabric flange and a lower fabric flange and in which the block is held in position by the upper and lower fabric flanges being fastened to each other in a line along the front edge of the disc.

7. A prosthesis according to claim 1 in which one continuation of the encapsulating fabric is provided and an other continuation of the fabric is provided, the one continuation of the fabric being interdigitated with said other continuation of the fabric by passing said other continuation of the fabric through a hole in said one continuation of the fabric.

8. A prosthesis according to claim 7 in which the interdigitation of the one continuation of the fabric and other continuation of the fabric defines the front of the prosthesis and in which an additional fabric element over the front of the prosthesis is provided.

9. A prosthesis comprising an element of elastomeric or visco-elastic material, the element being provided in a retaining fabric and in which a flange, suitable for attachment to vertebral bodies, is provided as a fabric continuation of the retaining fabric.

10. A prosthesis according to claim 10 in which the element of elastomeric or visco-elastic material is a block having an upper surface, a lower surface, front and back.

11. A prosthesis according to claim 10 in which the block provides substantially equivalent behavior to the nucleus pulposis of a natural disc, during compression, distraction, horizontal gliding, axial rotation, flexion and extension.

12. A prosthesis according to claim 10 in which the maximum width of the upper surface of the block is greater than the maximum width of the lower surface of the block.

13. A prosthesis according to claim 10 in which the minimum width of the upper surface of the block is greater than the minimum width of the lower surface of the block.

14. A prosthesis according to claim 10 in which the front thickness of the block is more than the back thickness of the block, preferably the front thickness of the block is more than the back thickness of the block, the front being the portion of the block nearer the front of the spine in use.

15. A prosthesis according to claim 10 in which the block is wider towards the front face than towards the rear face.

16. A prosthesis according to claim 10 in which the maximum length, l, from the front face of the block to the rear face of the block is between 10 and 15 mm.

17. A prosthesis according to claim 10 in which the maximum width of the upper surface of the block is between 12.5 and 16.5 mm.

18. A prosthesis according to claim 10 in which the minimum lower width of the block is between 8.5 and 12.5 mm.

19. A prosthesis according to claim 10 in which the maximum thickness of the block is between 2.5 and 5.5 mm.

20. A prosthesis according to claim 10 in which the block provides planar upper and lower surfaces, the upper surface having a greater width than the lower surface, the block having a greater thickness towards the front face than towards the rear face.

21. A prosthesis according to claim 10 in which the retaining fabric is formed from a piece of fabric having a first portion and a second portion, the first and second portions being joined by an integral part of the fabric, the first and second portions being folded into opposition to one another, the edges of the first and second portions being stitched to one another to provide a restraining/encapsulating portion of the fabric for the block.

22. A prosthesis according to claim 21 in which the retained fabric is provided with one or more further portions, the one or more further portions being attached to one or both of the first and second portions, the one or more further portions providing closure for a pocket receiving the block, the pocket being formed by the first and second portions.

23. A prosthesis according to claim 22 in which the one or more further portions provides a first further portion and a second further portion, in which one of the first or second further portions is provided with an aperture and the first and second further portions are interdigitated by passing the other of the first or second further portions through the aperture in the said one of the first or second further portions.

24. A prosthesis according to claim 23 in which the first further portion is attached to the vertebrae adjacent the second portion of the retaining fabric.

25. A prosthesis according to claim 22 in which the first and second portions form a pocket receiving the block, a portion of one of the further portions passing through an aperture or gap in one of the other further portions thereby forming a closure for the pocket receiving the block, a pad block being provided within the pocket between the block and the closure for the pocket receiving the block.

26. A prosthesis according to claim 25 in which the pad block is formed of the retaining fabric material and is integral with the retaining fabric material.

27. A prosthesis according to claim 26 in which the pad block is formed by folding a portion of the retaining fabric material.

28. A prosthesis according to claim 22 in which the prosthesis is provided with one or more flanges and in which the block component of the prosthesis acts as a replacement for the nucleus pulposis, the fabric provides a replacement for the annulus and the flanges provide a replacement for the anterior longitudinal ligament which is the ligament extending along that portion of the spine.

29. A surgical technique for providing a disc prosthesis, the technique comprising removing the natural disc and replacing the disc with a prosthesis, the prosthesis comprising a block of an elastomeric or visco-elastic material which is encapsulated by a textile fabric and in which a flange is provided as a fabric continuation of the encapsulating fabric, the flange being attached to one or more vertebral bodies.

30. A prosthesis according to claim 23 in which the second further portion is attached to the vertebrae adjacent the first portion of the retaining fabric.

* * * * *